United States Patent [19]
Au et al.

[11] Patent Number: 5,389,279
[45] Date of Patent: Feb. 14, 1995

[54] COMPOSITIONS COMPRISING NONIONIC GLYCOLIPID SURFACTANTS

[75] Inventors: Van Au, Peekskill, N.Y.; George Grudev, Hewitt, N.J.; Bijan Harirchian, South Orange, N.J.; Michael Massaro, Ridgefield Park, N.J.; Abid N. Khan-Lodhi, Hoole Chester, England

[73] Assignee: Lever Brothers Company, Division of Conopco, Inc., New York, N.Y.

[21] Appl. No.: 981,737

[22] Filed: Nov. 25, 1992

Related U.S. Application Data

[63] Continuation-in-part of Ser. No. 816,419, Dec. 31, 1991, abandoned.

[51] Int. Cl.$^6$ .................. C11D 9/00; C11D 9/30; C11D 1/18
[52] U.S. Cl. .................. 252/108; 252/117; 252/173; 252/542; 252/546; 252/548; 252/DIG. 6; 252/DIG. 13; 252/DIG. 14; 252/DIG. 16
[58] Field of Search .............. 252/108, 117, 542, 546, 252/548, 173, DIG. 6, DIG. 13, DIG. 14, DIG. 16

[56] References Cited

U.S. PATENT DOCUMENTS 2,752,334  6/1956  Walten ................. 260/211
5,009,814  4/1991  Kelkenberg et al. ....... 252/548

FOREIGN PATENT DOCUMENTS 2523962  9/1983  France .

OTHER PUBLICATIONS

Williams et al. Archives of Biochem & Biophysics, 195(1):145–151 (1979).
Chemical Abstract No. CA90(11):87774K.

*Primary Examiner*—Helen M. S. Sneed
*Assistant Examiner*—Nhat D. Phan
*Attorney, Agent, or Firm*—Ronald A. Koatz

[57] ABSTRACT

The present invention relates to personal product compositions which comprise aldobionamide (i.e. amide of an aldobionic acid or aldobionalactone) as a surfactant in the compositions. The aldobionamide compounds are based on compounds comprising two or more saccharide units. It is believed that such compounds pack less closely, are more water soluble than linear saccharides and thereby allow stable compositions to form more readily.

27 Claims, No Drawings

COMPOSITIONS COMPRISING NONIONIC GLYCOLIPID SURFACTANTS

CROSS REFERENCES

This is a continuation-in-part of Ser. No. 07/816,419, filed Dec. 31, 1991, now abandoned.

BACKGROUND OF THE INVENTION

The present invention relates to novel personal product or detergent compositions comprising glycolipids, and in particular to compositions comprising nonionic aldobionamides as surface active agents in the compositions. An aldobionamide is defined as the amide of an aldobionic acid (or aldobionolactone) and an aldobionic acid in turn is defined as a sugar substance (e.g., any cyclic sugar) in which the aldehyde group (generally found at the $C_1$ position on the sugar) has been replaced by a carboxylic acid. Aldobionamides may be based on compounds comprising two saccharide units, (e.g., lactobionamide or maltobionamide) or they may be based on compounds compromising more than two saccharide units as long as the polysaccharide has a terminal sugar unit with an aldehyde group available. There must, however, be at least two saccharide units because these materials pack less closely in the solid state making them more water soluble than a linear saccharide (e.g., a gluconamide or glucoheptonamide) thereby allowing a stable composition to form.

Most surfactants presently used in personal product and in detergent compositions are based on petrochemicals. Because of increased concern over environmental issues raised by use of petrochemicals and also because of the continually rising costs of these petrochemicals, it would be useful to develop surfactants which are instead derived from carbohydrates. These natural occurring compounds represent a source of renewable raw materials that are synthetically versatile, inexpensive, optically pure and environmentally friendly.

U.S. Pat. No. 2,752,334 to Walden teaches compounds which are the reaction products of aldonic acids (e.g., lactobionic acid) and fatty amines. The compound is said to be useful as an emulsifier in food composition.

In Williams et al., Archives of Biochem. and Biophysics, 195(1):145–151 (1979), there is described glycolipids prepared by linking aldobionic acids to alkylamine through an amide bond. Although it is said that these compounds, like all surfactants, form micelies, there is no teaching or suggestion of the use of these compounds in detergent or personal product compositions.

U.S. Pat. No. 5,009,814 teaches N-polyhydroxyalkyl fatty acid amides used as thickeners in aqueous surfactant systems having the formula

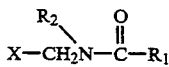

wherein $R_1$ is alkyl, $R_2$ is hydrogen, alkyl or alkyl hydroxide and X is a polyhydroxy group.

This is a completely different class of compounds than those of the invention. In these compounds the polyhydroxy group is separated by a methylene group attached to the Nitrogen atom rather than the carbonyl group resulting in an amide linkage that is reversed compared to the compounds of the invention. These compounds re prepared by the reaction of a monosaccharide suger amine with an alkyl ester of a fatty acid. The compounds of this invention are prepared by the reaction of disaccharide (or greater) sugar lactones with a fatty amine. Again, ours is completely different.

In addition, there is a series of Procter and Gamble applications teaching a number of compositions which comprise polyhydroxy amide. WO-92/06172, for example, teaches built liquid detergent compositions containing polyhydroxy acid amide. There are about 20 applications reciting various compositions containing the same polyhydroxy amide.

The polyhydroxy amide of each of these references is, like the compound of U.S. Pat. No. 5,009,814, a completely different compound from that of the invention. Again, the hydroxy group in each case is separated by a methylene group attached to the Nitrogen atom rather than the carbonyl group.

French Patent No. 82/05005 (Publication No. 2,523,962) teaches linear amides having the formula:

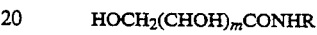

in which m is 2 to 6 and R is a linear or branched alkyl group having 6 to 18 carbons. These surfactants are said to be low foaming and must be ethoxylated or propoxylated by typical means for sufficient solubility.

The reference fails to teach the aldobionamide of the invention. Aldobionamides do not pack as closely in the solid state as aldonamides and are therefore more soluble (lower Krafft point) and higher foaming. To the extent that the reference teaches low foaming (suggesting low solubility and high Krafft point), the reference not only fails to teach or suggest the aldobionamides of the subject invention, but actually teaches away.

Accordingly, it would be greatly desirable to find carbohydrates, in particular aldobionamides, which can be successfully used as surfactants in personal product and detergent compositions.

BRIEF SUMMARY OF THE INVENTION

This invention relates to personal product or detergent compositions comprising glycolipid surfactants. In particular, the invention relates to the use of compositions comprising aldobionamide compounds used as surfactants or cosurfactants.

DETAILED DESCRIPTION OF THE INVENTION

The present invention relates to the use of personal product or detergent compositions comprising environmentally friendly surfactants, in particular environmentally friendly nonionic surfactants, such as aldobionamides.

Aldobionamides are defined as the amide of an aldobionic acid (or aldobionolactone) and an aldobionic acid is a sugar substance (e.g., any cyclic sugar comprising at least two saccharide units) wherein the aldehyde group (generally found at the $C_1$ position of the sugar) has been replaced by a carboxylic acid, which upon drying cyclizes do an aldonolactone.

An aldobionamide may be based on compounds comprising two saccharide units (e.g., lactobionamides or maltobionamides from the aldobionamide bonds), or they may be based on compounds comprising more than two saccharide units, as long as the terminal sugar in the polysaccharide has an aldehyde group. By definition an aldobionamide must have at least two saccharide units and cannot be linear. Disaccharide compounds such as lactobianomides or maltobionamides are preferred compounds. Other examples of aldobionamides (disaccharides) which may be used include cellobionamides, melibionamides and gentiobionamides.

A specific example of an aldobionamide which maybe used for purposes of the invention is the disaccharide lactobionamide set forth below:

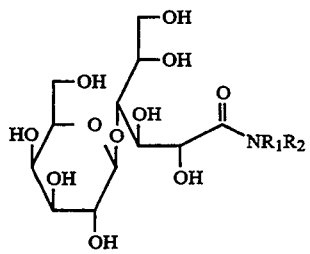

wherein $R_1$ and $R_2$ are the same or different and are selected from the group consisting of hydrogen; an aliphatic hydrocarbon radical (e.g., alkyl groups and alkene groups which groups may contain heteroatoms such as N, O or S or alkoxylated alkyl chains such as ethoxylated or propoxylated alkyl groups), preferably an alkyl group having 8 to 24, preferably 10 to 18 carbons; an aromatic radical (including substituted or unsubstituted aryl groups and arenes); a cycloaliphatic radical; an amino acid ester, ether amines and mixtures thereof, except that $R_1$ and $R_2$ cannot be hydrogen at the same time.

Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl.

Aromatic radicals are exemplified, for example, by benzyl.

Suitable mixed aliphatic aromatic radicals are exemplified by benzyl, phenyl ethyl, and vinyl benzyl.

Cycloaliphatic radicals are exemplified by cyclopentyl and cyclohexyl.

The aldobionamides used in the composition of the invention have been found to have properties (i.e., critical micelle concentrations; Krafft Point; foaming; detergency) indicating that they are equal to or better than other well known nonionic surfactants which are based on petrochemicals (e.g., alkoxylated surfactants from the Neodol TM series from Shell), thereby indicating that they can be a viable, environmentally friendly alternative to the use of more traditional nonionic surfactants. The aldobionamides also have lower Krafft points and greater solubility than the single saccharide linear counterpart.

While not wishing to be bound by theory, it is believed that the lower solubility of the aldobionamide is due to the sugar structure which prevents the close packing which occurs in linear monosaccharide aldonamides such as gluconamides. The greater number of hydroxyl groups also probably help to make the aldobionamides more soluble.

In addition, the surfactants of the invention may be used as cosurfactants with other nonionic surfactants or with other surfactants (e.g., cationic, anionic, zwitterionic, amphoteric) used in personal product or detergent formulations.

COMPOSITIONS

The personal product compositions of the invention may be, for example, toilet bar compositions, facial or body cleansing compositions, shampoos for hair or body, conditioners, cosmetic compositions, dental compositions, light duty liquids, shaving creams and shaving lotion compositions, and shower gel compositions.

In one embodiment of the invention, the aldobionamide surfactant of the invention may be used, for example, in a toilet bar (i.e., soap and/or detergent bar) formulation.

Typical toilet bar compositions are those comprising fatty acid soaps used in combination with a detergent other than fatty acid soap and free fatty acids. It should be noted that the composition may comprise fatty acid soap and may be based merely on actives other than fatty acid soap. Mildness improving salts, such as alkali metal salt or isethionate, are also typically added. In addition other ingredients, such as germicides, perfumes, colorants, pigments, suds-boosting salts and antimushing agents may also be added.

Fatty acid soaps are typically alkali metal or alkanol ammonium salts of aliphatic alkane or alkene monocarboxylic acids. Sodium, potassium, mono-, di- and triethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons. They may be described as alkali metal carboxylates of acrylic hydrocarbons having about 12 to 22 carbons.

Examples of soap which may be used may be found in U.S. Pat. No. 4,695,395 to Caswell et al. and U.S. Pat. No. 4,260,507 (Barrett), both of which are incorporated herein by reference.

In a soap-based bar, fatty acid soaps will generally comprise greater than 25% of the composition, generally from 30-95%. Preferably, the amount of soap will range from 40% to 70% by weight of the composition. In a bar based on other actives, soap may comprise 0-50% by weight. In general $C_8$ to $C_{24}$ fatty acid comprises 5-60% of the composition.

The compositions will also generally comprise a non-soap detergent which is generally chosen from anionic, nonionic, cationic, zwitterionic or amphoteric synthetic detergent materials or mixtures thereof. These surfactants are all well known in the art and are described, for example, in U.S. Pat. Nos. 4,695,395 and 4,260,507 discussed above. One preferred non-soap anionic is a $C_8$–$C_{22}$ akyl isethionate. These ester may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 40% of the compositions.

A preferred salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betain compounds or ether sulphates. These also may be present at 0.1 to 50% of the composition, preferably 0.5% to 25%.

The sulfate ester surfactant may comprise 0.01 to 45% by weight of the composition (as the monoester), preferably 25% to 40%, and 0.01% to 10% of the composition (as the diester), preferably 0.01% to 5%.

Other optional ingredients which may be present in toilet bar compositions are moisturizers such as glycerin, propylene glycol, sorbitol, polyethylene glycol, ethoxylated or methoxylated ether of methyl glucose etc.; water-soluble polymers such as collagens, modified cellulases (such as Polymer JR ®), guar gums and polyacrylates; sequestering agents such as citrate, and emollients such as silicones or mineral oil. another useful set of ingredients are various cosurfactants and non-soap detergents.

In a second embodiment of the invention, the aldobionamide surfactant of the invention may be present in a facial or body cleansing composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener (e.g., magnesium aluminum silicate, carbopol), conditioners, water soluble polymers (e.g., carboxymethyl cellulose), dyes, hydrotropes brighteners, perfumes and germicides.

The fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al, hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (eg., methyl gluceth-20) and ethoxylated/propoxylated ethers of lanolin alcohol (e.g., Solulan-75).

Preferred moisturizers are coco and tallow fatty acids. Some other preferred moisturizers are the nonoclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner, Cosmetics & Toiletries, May 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co, Inc.; Jaguar C-14-S made by Stein Hall; Mirapol A15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. a preferred nonionic hydroxypropyl guar gum material is Jaguar ® HP-60 having molar substitution of about 0.6. another class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ® 300 and 400 made by Staley, Inc.

A more complete list of cationic polymers useful in the present invention is described in U.S. Pat. No. 4,438,095, to Grollier/allec, issued Mar. 20, 1984, incorporated herein by reference. Some of the more preferred cationics are listed in Col. 3, Section 2; Col. 5, section 8; Col. 8, section 10; and Col. 9, lines 10–15 of the Grollier/allec patent, incorporated herein by reference.

In a third embodiment of the invention, the aldobionamide surfactant of the invention may be used, for example, in a bar or body shampoo. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g. selenium sulfide.

The compositions all may also optionally comprise a suspending agent, for example, any of several acyl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmirate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc., offers xanthan gum as KeltrolR.

A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R.T. Vanderbilt Company, Inc. Mixtures of suspending agents are also suitable for use in the compositions of this invention.

Other useful thickening agents are the cross-linked polyacrylates such as those manufactured by B. F. Goodrich and sold under the Carbopol ® tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials. Other materials include alginates, polyacrylic acids, polyethylene glycol and starches, among many others. The nonionic polymers are discussed in detail in *Industrial Gums*, edited by Roy L. Whistler, academic Press, Inc., 1973, and *Handbook of Water-Soluble Gums and Resins*, edited by Robert L. Davidson, McGraw-Hill, Inc., 1980. Both of these books in their entirety are incorporated herein by reference.

When included, the nonionic polymer is used at a level of from about. 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylarly siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The siloxane viscosity can be measured by means of a glass capillary viscometer as set forth in Dow Corning Corporate Test Method CTM0004, July 20, 1970. Preferably the viscosity of the these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff; U.S. Pat. No. 4,364,837, Pader; and British Patent 849,433, Woolston. all of these patents are incorporated herein by reference. also incorporated herein by reference is Silicon Compounds, distributed by Petrarch Systems, Inc., 1984. This reference provides a very good listing of suitable silicone materials.

Another silicone material useful is silicone gum. Silicone gums are described by Petrarch and others including U.S. Pat. No. 4,152,416, May 1, 1979, Spitzer, et al., and Noll, *Chemistry and Technology of Silicones,* New York, academic Press, 1968. Useful silicone gums are also described in General Electric Silicone Rubber Product Data Sheets SE 30, SE 33, SE 54 and SE 76. all of these references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as Pluronic F88 offered by BaSa Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5% to about 5.0%, of the composition.

A typical shampoo composition might comprise (percentages by weight):

(1) Aldobionamide 5–15%;
(2) Anionic coactive 0–10%;
(3) Amphoteric coactive 0–10%;
(4) Lauramide MEA 0–5%;
(5) Thickener 0–5%;
(6) Fragrance 0–2 %;
(7) Preservative 0–1%; and
(8) Remainder water In a fourth embodiment of the invention, the aldobionamide surfactant of the invention may be used in a conditioner composition such as is taught and described in U.S. Pat. No. 4,913,828 to Caswell et al. which is hereby incorporated by reference.

More particularly, conditioner compositions are those containing a conditioning agent (e.g. alkylamine compounds) such as those described in U.S. Pat. No. 4,913,828.

In a fifth embodiment of the invention, the surfactant may be used in a cosmetic composition, such as is taught and is described in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar $C_{13}$ S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1, 3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity from 1 to <0.9, preferably to <0.85 and most preferably <0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1, 2-diol, butane-1.3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazoles, quinine salts, quinoline derivatives, hydroxy or methoxy substituted benzophenones, uric or vilouric acid, tannic acid and its derivatives, hydroquinone, and benzophenones.

In a sixth embodiment of the invention, the surfactant may be used in a toothpaste composition such as is taught and is described in U.S. Pat. No. 4,935,227 to Duckworth, which is hereby incorporated by reference.

Such compositions generally comprise abrasive gels (e.g. calcium carbonate), oral therapeutic agents (e.g., flourine containing compound), coactives, flavoring agents, sweetening agents, humectants and binding or thickening gels.

Preferred toothpastes of this invention comprise 0 to 1.5% by weight of anionic surfactant. In more preferred products the amount of anionic surfactant is 0 to 1% by weight with most preferred amounts being 0 to 0.75% by weight.

Toothpastes of this invention may include other surfactants, especially non-ionic surfactants.

Toothpaste of the invention will also comprise the usual additional ingredients in particular humectant binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose, cross-linked polyacrylates and xanthan gum. Others include natural gum binders such as gum tragacanth, gum karaya and gum arabic, Irish moss, alginates, and carrageenans. Silica thickening agents include the silica aerogels and various precipitated silicas. Mixtures of binders and thickeners may be used. The amount of binder and thickening agent included in a toothpaste is generally between 0.1 and 15% by weight.

In a seventh embodiment of the invention, the compound of the invention may be used in a light duty liquid detergent composition such as those taught in U.S. Pat. No. 4,671,894 to Lamb et al, U.S. Pat. No. 4,368,146 to Aronson et al., and U.S. Pat. No. 4,555,360 to Bissett et al., all of which are hereby incorporated by reference into the subject application.

Generally such compositions comprise a mixture of sulphate and sulphonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g. ethylene glycol distearate), thickeners (e.g., guar gum), antibacterial agents, antitarnish agents, heavy metal chelators (e.g. ETDA), perfumes and dyes.

In an eighth embodiment of the invention the compound of the invention may be used in underarm deodorant/antiperspirant compositions such as those taught in U.S. Pat. No. 4,919,934 to Deckner, U.S. Pat. No. 4,944,937 to McCall and U.S. Pat. No. 4,944,938 to Patini, all of which patents are hereby incorporated by reference.

Such compositions generally comprise a cosmetic stick (gel or wax) composition which in turn generally comprises one or more liquid base materials (e.g., water, fatty acid and fatty alcohol esters, water-insoluble ethers and alcohols, polyorganosiloxanes); a solidifying agent for solidifying the liquid base; and an active component such as bacteriostats or fungistats (for antideodorant activity) or astringent metallic salts (for antiperspirant activity).

These compositions may also comprise hardeners, strengtheners, emollients, colorants, perfumes, emulsifiers and fillers.

In another embodiment of the invention, the aldobionamide surfactants of the invention may be used in shaving cream or shaving lotion compositions. A typical shaving cream composition is set forth below:

| Leather Shaving Cream | |
|---|---|
| Ingredients | % by Weight |
| Stearic acid | 20–40 |
| Coconut oil or fatty acid | 6–10 |
| Aldobionamide | 1–45 |
| Glycerol | 5–15 |
| Potassium hydroxide | 2–6 |
| Sodium hydroxide | 1–3 |
| Vegetable or mineral oil | 1–5 |
| Water | to balance |

A typical brushless shaving cream composition is also set forth below:

| Ingredients | % by Weight |
|---|---|
| Glyceryl monostearate | 10–35 |
| Mineral oil | 5–15 |
| Aldobionamide | 1–45 |
| Glycerol | 1–10 |
| Water | to balance |

| Ingredients | % by Weight |
|---|---|
| Cellulosic alkyl ether | 70–75% |
| Glycerol | 3–10 |
| Aldobionamide | 1–5 |
| Mineral oil | 10–20 |
| Water | to balance |

In yet another embodiment of the invention, the aldobionamide surfactant may be used in shower gel compositions. A typical shower gel composition is set forth below:

| Ingredients | % by Weight |
|---|---|
| Sodium cocoyl isethionate | 5–10 |
| Sodium ether lauryl sulfate | 2–5 |
| Aldobionamide | 1–45 |
| Coconut amidopropyl betaine | 8–15 |
| Ethylene glycol distearate | 4–10 |
| Isopropyl palmitate | 0.5–1 |
| Moisturizing factor | 0.25–0.5 |
| Preservative | 0.05–0.1 |
| Sodium chloride | 3–5 |
| Water | to balance |

While various compositions are described above, these should not be understood to be limiting as to what other personal product compositions may be used since other compositions which may be known to those of ordinary skill in the art are also contemplated by this invention.

In addition, the surfactants of the invention may also be used in cleansing or detergent compositions such as heavy duty liquids or detergent powders. Examples of liquid detergent compositions are described in U.S. Pat. No. 4,959,179 to Aronson et al. and examples of powdered detergent compositions are described in U.S. Pat. No. 4,929,379 to Oldenburg et al. Both these patents are hereby incorporated by reference into the subject application.

The liquid detergent compositions of the invention may be built or unbuilt and may be aqueous or nonaqueous. The compositions generally comprise about 5%–70% by weight of a detergent active material and from 0% to 50% of a builder. The aldobionamide of the invention may be the sole surfactant in the formulation or it may be a cosurfactant in which it is used in combination with a surfactant selected from the group consisting of soap, anionics, nonionics, cationics and zwitterionic surfactants. If used as a cosurfactant, the lactobionamide may comprise 5 to 99% preferably 5 to 50% of the active system. The liquid detergent compositions of the invention may further comprise an amount of electrolyte (defined as any water-soluble salt) whose quantity depends on whether or not the composition is structured. By structured is meant the formation of a lamellar phase sufficient to endow solid suspending capability.

More particularly, while no electrolyte is required for a non-structured, non-suspending composition, at least 1%, more preferably at least 5% by weight and most preferably at least 15% by weight electrolyte is used. The formation of a lamellar phase can be detected by means well known to those skilled in the art.

The water-soluble electrolyte salt may be a detergency builder, such as the inorganic salt sodium tripolyphosphate or it may be a non-functional electrolyte such as sodium sulphate or chloride. Preferably, whatever builder is used in the composition comprises all or part of the electrolyte.

The liquid detergent composition generally further comprises enzymes such as proteases, lipases, amylases and cellulases which, when present, may be used in amounts from about 0.01 to 5% of the compositions. Stabilizers or stabilizer systems may be used in conjunction with enzymes and generally comprise from about 0.1 to 15% by weight of the composition.

The enzyme stabilization system may comprise calcium ion, boric acid, propylene glycol and/or short chain carboxylic acids. The composition preferably contains from about 0.01 to about 50, preferably from about 0.1 to about 30, more preferably from about 1 to about 20 millimoles of calcium ion per liter.

When calcium ion is used, the level of calcium ion should be selected so that there is always some minimum level available for the enzyme after allowing for complexation with builders, etc., in the composition. Any water-soluble calcium salt can be used as the source of calcium ion, including calcium chloride, calcium formate, calcium acetate and calcium propionate. A small amount of calcium ion, generally from about 0.05 to about 2.5 millimoles per liter, is often also present in the composition due to calcium in the enzyme slurry and formula water.

Another enzyme stabilizer which may be used is propionic acid or a propionic acid salt capable of forming propionic acid. When used, this stabilizer may be used in an amount from about 0.1% to about 15% by weight of the composition.

Another preferred enzyme stabilizer is polyols containing only carbon, hydrogen and oxygen atoms. They preferably contain from 2 to 6 carbon atoms and from 2 to 6 hydroxy groups. Examples include propylene glycol (especially 1,2 propanediol which is preferred), ethylene glycol, glycerol, sorbitol, mannitol and glucose. The polyol generally represents from about 0.5% to about 15%, preferably from about 1.0% to about 8% by weight of the composition.

The composition herein may also optionally contain from about 0.25% to about 5%, most preferably from about 0.5% to about 3% by weight of boric acid. The boric acid may be, but is preferably not, formed by a compound capable of forming boric acid in the composition. Boric acid is preferred, although other compounds such as boric oxide, borax and other alkali metal borates (e.g. sodium ortho-, meta- and pyroborate and sodium pentaborate) are suitable. Substituted boric acids (e.g., phenylboronic acid, butane boronic acid and a p-bromo phenylboronic acid) can also be used in place of boric acid.

On especially preferred stabilization system is a polyol in combination with boric acid. Preferably, the weight ratio of polyol to boric acid added is at least 1, more preferably at least about 1.3.

With regard to the detergent active, the detergent active material may be an alkali metal or alkanolamine soap or a 10 to 24 carbon atom fatty acid, including polymerized fatty acids, or an anionic, a nonionic, cationic, zwitterionic or amphoteric synthetic detergent material, or mixtures of any of these.

Examples of the anionic synthetic detergents are salts (including sodium, potassium, ammonium and substituted ammonium salts) such as mono-, di- and triethanolamine salts of 9 to 20 carbon alkylbenzenesulphonates, 8 to 22 carbon primary or secondary alkanesulphonates, 8 to 24 carbon olefinsulphonates, sulphonated polycarboxylic acids prepared by sulphonation of the pyrolyzed product of alkaline earth metal citrates, e.g., as described in British Patent specification, 1,082,179, 8 to 22 carbon alkylsulphates, 8 to 24 carbon alkylpolyglycol-ethersulphates, -carboxylates and -phosphates (containing up to 10 moles of ethylene oxide); further examples are described in "Surface Active Agents and Detergents" (vol. I and II) by Schwartz, Ferry and Bergh. Any suitable anionic may be used and the examples are not intended to be limiting in any way.

Examples of nonionic synthetic detergents which may be used with the invention are the condensation products of ethylene oxide, propylene oxide and/or battalion oxide with 8 to 18 carbon alkylphenols, 8 to 18 carbon fatty acid amides; further examples of nonionics include tertiary amine oxides with 8 to 18 carbon alkyl chain and two 1 to 3 carbon alkyl chains. The above reference also describes further examples of nonionics.

The average number of moles of ethylene oxide and/or propylene oxide present in the above nonionics varies from 1–30; mixtures of various nonionics, including mixtures of nonionics with a lower and a higher degree of alkoxylation, may also be used.

Examples of cationic detergents which may be used are the quaternary ammonium compounds such as alkyldimethylammonium halogenides.

Examples of amphoteric or zwitterionic detergents which may be used with the invention are N-alkylamine acids, sulphobetaines, condensation products of fatty acids with protein hydrolysates; but owing to their relatively high costs they are usually used in combination with an anionic or a nonionic detergent. Mixtures of the various types of active detergents may also be used, and preference is given to mixtures of an anionic and a nonionic detergent active. Soaps (in the form of their sodium, potassium and substituted ammonium salts) of fatty acids may also be used, preferably in conjunction with an anionic and/or nonionic synthetic detergent.

Builders which can be used according to this invention include conventional alkaline detergency builders, inorganic or organic, which can be used at levels from 0% to about 50% by weight of the composition, preferably from 1% to about 20% by weight, most preferably from 2% to about 8%.

Examples of suitable inorganic alkaline detergency builders are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetates and N-(2 hydroxyethyl)-nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1,1diphosphonic acid; sodium, potassium and lithium salts of methylene diphosphonic acid; and sodium, potassium and lithium salts of ethane-1,1,2-triphosphonic acid. Other examples include the alkali methal salts of ethane-2-carboxy-1,1-diphosphonic acid hydroxymethanediphosphonic acid, carboxylidiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water soluble salts of polycarboxylate polymers and copolymers as described in U.S. Pat. No. 3,308,067.

In addition, polycarboxylate builders can be used satisfactorily, including water-soluble salts of mettitic acid, citric acid, and carboxymethyloxysuccinic acid and salts of polymers of itaconic acid and maleic acid. Other polycarboxylate builders include DPA (dipicolinic acid) and ODS (oxydisuccinic acid). Certain zeolites or aluminosilicates can be used. One such aluminosilicate which is useful in the compositions of the invention is an amorphous water-insoluble hydrated compound of the formula $Na_x(_yAlO_2.SiO_2)$, wherein x is a number from 1.0 to 1.2 and y is 1, said amorphous material being further characterized by a $Mg++$ exchange capacity of from about 50 mg eq. $CaCO_3$/g. and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y.(SiO_2)]xH_2O$, wherein z and y are integers of at least 6; the molar ratio of z and y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grams/gallon/minute/-gram. These synthetic aluminosilicates are more fully described in British Pat. No. 1,429,143.

In addition to the ingredients described hereinbefore, the preferred compositions herein frequently contain a series of optional ingredients which are used for the known functionality in conventional levels. While the detergent compositions are generally premised on aqueous, enzyme-containing detergent compositions, it is frequently desirable to use a phase regulant. This component together with water constitutes then the solvent matrix for the claimed liquid compositions. Suitable phase regulants are well-known in liquid detergent technology and, for example, can be represented by hydrotropes such as salts of alkylarylsulfonates having up to 3 carbon atoms in the alkylgroup, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%, the sum of phase regulant and water is normally in the range from 35% to 65%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

The beneficial utilization of the claimed compositions under various usage conditions can require the utilization of a suds regulant. While generally all detergent suds regulants can be utilized, preferred for use herein are alkylated polysiloxanes such as dimethylpolysiloxane, also frequently termed silicones. The silicones are frequently used in a level not exceeding 0.5%, most preferably between 0.01% and 0.2%.

It can also be desirable to utilize opacifiers inasmuch as they contribute to create a uniform appearance of the concentrated liquid detergent compositions. Examples of suitable opacifiers include: polystyrene commercially known as LYTRON 621 manufactured by Monsanto Chemical Corporation. The opacifiers are frequently used in an amount from 0.3% to 1.5%.

The compositions herein can also contain known antioxidants for their known utility, frequently radical scavengers in the art established levels, i.e., 0.001% to 0.25% (by reference to total composition). These antioxidants are frequently introduced in conjunction with fatty acids.

The liquid detergent compositions of the invention may also contain deflocculating polymers such as described in U.S. Ser. No. 664,513, filed Mar. 5, 1991, hereby incorporated by reference.

When the liquid composition is an aqueous composition, the balance of the formulation consists of an aqueous medium. When it is in the form of a non-aqueous composition, the above ingredients make up for the whole formulation (a non-aqueous composition may contain up to about 5% water).

An ideal liquid detergent composition might contain (all percentages by weight):
(1) 5–70% detergent active (or active mixture);
(2) 0–50% builder;
(3) 0–40% electrolyte
(4) 0.01–5% enzyme;
(5) 0.1–15% enzyme stabilizer;
(6) 0–20% phase regulant; and
(7) remainder water and minors The detergent composition of the invention might also be a powdered detergent composition.

Such powdered compositions generally comprise from about 5–40% of a detergent active system which generally consists of an anionic, a nonionic active, a fatty acid soap or mixtures thereof; from 20–70% of an alkaline buffering agent; up to about 40% builder and balance minors and water.

The alkaline buffering agent may be any such agent capable of providing a 1% product solution with a pH of above 11.5 or even 12. Advantageous alkaline buffering agents are the alkalimetal silicates, as they decrease the corrosion of metal parts in washing machines, and in particular sodium orthometa- or di-silicates, of which sodium metasilicate is preferred. The alkaline buffering agent is present in an amount of from 0 to 70% by weight, preferably from 0 to 30% by weight.

In addition the compositions of the invention can and normally will contain detergency builders in an amount of up to 40% by weight and preferably from 5 to 25% by weight of the total composition.

Suitable builders include sodium, potassium and ammonium or substituted ammonium pyro- and tri-polyphosphates, -ethylene diamine tetraacetates, -nitrilotriacetates, -etherpolycarboxylates, -citrates, -carbonates, -orthophosphates, -carboxymethyloxysuccinates, etc. Other builders include DPA and ODS. Also less soluble builders may be included, such as e.g., an easily dispersible zeolite. Particularly preferred are the polyphosphate builder salts, nitrilotriacetates, citrates, carboxymethyloxysuccinates and mixtures thereof.

Other conventional materials may be present in minor amounts, provided they exhibit a good dissolving or dispersing behavior; for example sequestering agents, such as ethylenediamine tetraphosphonic acid; soil-suspending agents, such as sodiumcarboxymethylcellulose, polyvinylpyrrolidone or the maleic anhydride/vinylmethylether copolymer, hydrotropes; dyes; perfumes; optical brighteners; alkali-stable enzymes; germicides; anti-tarnishing agents; lather depressants; fabric softening agents; oxygen- or chlorine-liberating bleaches, such as dichlorocyanuric acid salts or alkalimetal hypochlorides.

The remainder of the composition is water, which is preferably present in hydrated form, such as e.g., in the form of silicate 5 aq.

An ideal powdered detergent composition might contain the following (all percentages by weight):
(1) 5–40% detergent active (or active mixture);
(2) 0–40% builder;
(3) 0–30% buffer salt;
(4) 0–30% sulfate;
(5) 0–20% bleach system;
(6) 0–4% enzyme;
(7) minors plus water to 100%.

The invention is set forth in greater detail in the examples which follow below. These examples are merely to illustrate the invention and are not intended to be limiting in any way.

EXAMPLES

Methodology for Preparation of N-Alkyl Lactobionamides

Synthesis of N-Alkyl Lactobionamides

N-alkyl lactobionamides were synthesized by the reaction of commercially available lactobiono-1, 5-lactone with various linear alkylamines either in anhydrous DMF, methanol, or neat as shown below:

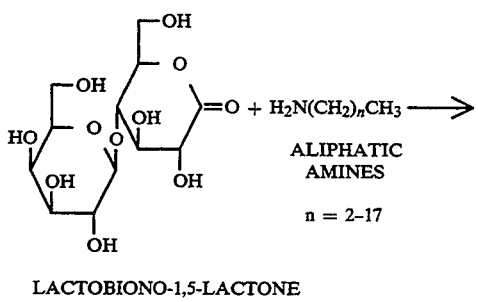

LACTOBIONO-1,5-LACTONE

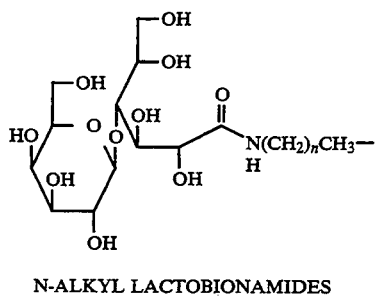

N-ALKYL LACTOBIONAMIDES

Dimethyl Formamide as Solvent

This procedure involved dissolving the lactobiono-1, 5-lactone in minimum amount of anhydrous DMF at 80° C. followed by the addition of 1 eq. of alkylamine. Although this procedure provided excellent yields, the products were colored and repeating washing with solvent was necessary.

Methanol as Solvent

This procedure was exercised as described in U.S. Pat. No. 2,752,334 to National Diary. Lactobiono-1,5-lactone and the alkylamines were refluxed in methanol and the corresponding colored products were isolated in moderate yields. Continuous washing with solvent was required for decoloration of the products.

Non-solvent Method

Excess alkylamines and lactobiono-1, 5-lactone were heated at 90°-100° C. with vigorous stirring. The colored products were isolated in moderate yields.

Examples of each of these methods is set forth in greater detail below:

Alternative Synthesis for N-tetradecyl lactobionamide

In a 5 L three necked round bottom flask equipped with a condenser and mechanical stirrer, lactobiono-1,5-lactone (400 g) was dissolved in warm methanol (3.5 L, 50°-55° C.). Melted tetradecylamine (1.0 eq, 272 g) was then added. The reaction was cooled to room temperature followed by stirring overnight to allow complete crystallization. The desired white product was filtered and recrystallized from methanol in 91% (550 g) isolated yield. The methanol filtrate contained a mixture of N-tetradecy lactobionamide and tetradecylammonium lactonbionate.

The above procedure can also be used to isolate other N-alkyl aldonamides.

EXAMPLE 1

Preparation of N-decyl Lactobionamide 20 g of lactobiono-1,5-lactone (1 eq) was dissolved in 40 ml of anhydrous DMF at 75°-80° C., 8.8 g (1 eq) of decylamine was added. The reaction was maintained at 75°-80° C. with stirring for 30 minutes. The reaction was cooled, ethyl ether (150 ml) was added, the product was filtered and washed with ethyl ether (2 x 100 ml). Recrystallization from methanol/ethyl ether gave 80% yield of the desired product.

EXAMPLE 2

Preparation of N-dodecyl Lactobionamide 30 g of lactobiono-1,5-lactone (1 eq) was dissolved in 70 ml of anhydrous DMF at 75°-80° C. 15.85 g (1 eq) dodecylamine was added, the reaction mixture was kept stirring at 70°-80° C. for 30 minutes. The reaction was allowed to cool, ethyl ether (200 ml) was added. The product was filtered and washed with ethyl ether (2×150 ml) and recrystallization from MeOH gave 90% of the desired product.

EXAMPLE 3

Preparation of N-tetradecyl Lactobionamide

Lactobiono-1,5-lactone (20 g, 1 eq) was dissolved in 60 ml of anhydrous DMF at 65° C. 12.5 g of tetradecylamine (1 eq) was added, the reaction Was stirred at 65° C. for 30 minutes. The reaction mixture was cooled, ethyl ether (2×150 ml) was added. The product was filtered and washed with ethyl ether. Recrystallization from methanol yielded 92% of the desired product.

EXAMPLE 4

Preparation of N-hexadecyl Lactobionamide

The same procedure was employed as in Example 3 using 10 g of lactobiono-1,5-lactone (1 eq) and 7.1 g of hexadecylamine (1 eq). Recrystallization from MeOH yielded 90% of the desired product.

EXAMPLE 5

Preparation of N-propyl Lactobionamide 5 g of lactobiono-1,5-lactone (1 eq) was dissolved in 20 ml of anhydrous DMF at 80° C. 0.86 g propylamine (1 eq) was added. The reaction was stirred at 80° C. for 30 minutes. The solvent was removed. The residue was washed with ethyl ether (2×50 ml). Recrystallization from MeOH/ethyl ether gave 80% yield of the desired product.

EXAMPLE 6

Preparation of N-pentyl Lactobionamide

Lactobiono-1,5-lactone (5 g, 1 eq) and amylamine (1.41 g, 1 eq) was heated in 30 ml of anhydrous methanol to reflux for one hour. Small amount of activated charcoal was added, filtered when hot. The solvent was removed, the residue was washed with ethyl ether followed by acetone and dried. The yield was 50%.

EXAMPLE 7

Preparation of N-octyl Lactobionamide

Lactobiono-1,5-lactone (10 g, 1 eq) and octylamine (7.6 g, 2 eq) was heated to 90° C. for 30 minutes with vigorous stirring. The reaction was allowed to cool, washed with (2×150 ml) of ethyl ether. Recrystallization twice from MeOH/ethyl ether gave 80% yield of the desired product.

EXAMPLE 8

Preparation of N-dodecyl Lactobionamide 20 g of lactobiono-1,5-lactone and 11 g of dodecylamine (1 eq) was dissolved in 200 ml of methanol by heating it to reflux temperature. The reaction mixture was allowed to stir at room temperature overnight. The product was filtered, washed with methanol (100 ml), followed by ethyl ether (2×75 ml). Recrystallization from MeOH gave 57% yield of the desired product.

EXAMPLE 9

N-lactobionyl dodecyl glycinate 9.0 g of dodecyl glycinate hydrochloride was dissolved in 50 ml of anhydrous methanol by gentle heating, 16 ml of 2.0M methanolic ammonia was added, followed by addition of 10.9 g (1 eq) of lactobiono-1,5-lactone. The reaction mixture was heated to reflux for 2.0 h and activated charcoal was added and the mixture was filtered hot. The solvent was removed, the product was washed with ethyl ether and dried in a vacuum oven at 40° C. with $P_2O_5$ to give a yield of approximately 75%.

EXAMPLE 10

N-lactobionyl dodecyl B-alanate

The same procedure was employed as described above for the dodecyl glycinate form by reacting 3.0 g of dodecyl β-alanate hydrochloride with 3.45 of lactobiono-1,5-lactone in anhydrous MeOH. The yield was approximately 70%.

EXAMPLE 11

N-decyloxypropyl lactobionamide 50 g of Lactobiono-1,5-lactone was dissolved in 400 ml of methanol (50°–55° C.), decyloxypropylamine (Adogen® 180, 31.6 g, 1 eq) was added. The reaction was cooled to room temperature followed by stirring overnight. The solvent was removed (250 ml) and acetone (400 ml) was added. The product was filtered, washed with acetone and dried in vacuum oven at 40° C. The yield was approximately 80%.

Preparation of coco lactobionamide

Lactobiono-1,5-lactone (400 g,leq) was dissolved in methanol(2.31,50 C) with stirring, cocoamine (Adogen 160-D{R},211.8 g,leq) was added slowly over 10 minutes. After the addition completed, the reaction mixture was let stirred for additional 10 minutes follow by seeding the solution with small ammount of coco lactobionamide and let stirred over night at room temperature. The product was filtered, washed with with warm acetone twice and dried in vaccum oven at 40 C. The yield was 394 g.

EXAMPLE 13

Preparation of tallow lactobionamide

Lactobiono-1,5-lactone (200 g,leq) was dissolved in methanol (45 C,1.31) tallow amine (Adogen 170-D{R},144.7 g,leq) was added slowly in several portions. After the addition completed, the reaction mixture was stirred over night at room temperature. The product was filtered, washed with isopropanol follow by acetone and dried in vaccum oven at 40 C. The yield was 270 g.

EXAMPLE 14

Preparation of oleyl lactobionamide

Lactobiono-1,5-lactone (100 g,leq)was dissolved in methanol (50 C,400ml) oleylamine (Adogen 172-D {R},76.1 g,leq) was added slowly. After the addition completed, the reaction was let stir at room temperature over night. The product was filtered, washed with acetone 2× and dried in vaccum oven at 40 C. The yield was 130 g.

EXAMPLE 15

Preparation of N-dodecyl-N-methyl lactobionamide

Lactobiono-1,5-lactone (8.7 g,leq) was dissolved in methanol (50 C,30ml) N-dodecylmethylamine (5 g,leq) was added. The reaction was let stir over night at room temperature. The solvent was removed, the product was washed with acetone and dried in vaccum oven at 40 C. The yield was 12 g.

SURFACTANCY

In order to determine the effectiveness of these compounds as a surfactant, various physical properties (i.e., CMC, Krafft point, foam height, Zein dissolution, detergency) of the surfactant, which are associated with how "good" a surfactant is, were measured. In particular, these properties were compared to the well known and commonly used ethoxylated surfactants. The results of these various measurements are set forth in Examples 16–19 below.

EXAMPLE 16

Critical Micelle Concentration (CMC)

The CMC is defined as the concentration of a surfactant at which it begins to form micelles in solution. Specifically materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. another means of minimizing the free energy can be achieved by the aggregation of these surface-active molecules into clusters or micelles with their hydrophobic groups directed toward the interior of the cluster and their hydrophilic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e., lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC.

The CMC of various surfactants were measured and the results set forth below:

| Surfactant | CMC |
| --- | --- |
| n-Dodecyl-β-D-glucoside | $1.9 \times 10^{-4}$M (25° C.) |
| n-$C_{12}$ alcohol (with 7 EO's) | $7.3 \times 10^{-5}$M (40° C.) |
| $C_{10}$-lactobionamide | — |
| $C_{12}$-lactobionamide | $4.2 \times 10^{-4}$M (45° C.) |
| $C_{14}$-lactobionamide | $4.5 \times 10^{-5}$M (45° C.) |

As the table above indicates, the CMC values of N-decyl and tetradecyl lactobionamides were found to be comparable to that of N-Dodecyl-β-D glucoside and heptaethoxylated dodecyl alcohol. These values indicate that the lactobionamide surfactants are comparable to other widely used nonionic surfactants.

EXAMPLE 17

Krafft Points

The temperature at and above which surfactants begin to form micelles instead of precipitates is referred to as Krafft point (Tk) and at this temperature the solubility of a surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Krafft point described above.

While not wishing to be bound by theory, it is believed that lower Krafft points are indicative of a surfactant being more soluble in aqueous system.

The Krafft point of various lactobionamides is set forth as follows:

|  | Krafft Point |
| --- | --- |
| $C_{10}$ - lactobionamide | 0° C. |
| $C_{12}$ - lactobionamide | 38° C. |
| $C_{14}$ - lactobionamide | 46° C. |

This table indicates that the $C_{10}$ chain length surfactants would tend to have better surfactancy properties than $C_{12}$ and $C_{14}$ counterparts at lower temperatures.

EXAMPLE 18

Foam Height

Foam is an important attribute in many consumer products (e.g., consumer products). Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles, G. D. Am. Soc. for Testing Material Method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam production (measured initially) and foam stability (the height after 10 minutes) are reported. All of the foaming was achieved at 45° C. in water with 120 ppm hardness. The foam height is represented in millimeters (mm).

The initial foam height and height after 10 minutes (i.e. foam stability) for various surfactants and mixtures of surfactants is set forth below:

|  | Initial Height | After 10 Minutes |
| --- | --- | --- |
| $C_{10}$ lactobionamide | 150 | 5 |
| $C_{12}$ lactobionamide | 153 | 20 |
| $C_{14}$ lactobionamide | 145 | 140 |
| Mixture of $C_{12}$ and $C_{14}$ | 155 | 135 |
| Neodol 91-6 ($C_9$-$C_{11}$ alcohol plus 6 EO) | 130 | 5 |

As seen above, the $C_{14}$ lactobionamide and the mixture of $C_{12}$ and $C_{14}$ lactobionamides shows best foam stability.

It should be noted that it is very unusual to get this type of foam stability with other nonionics.

Detergency Evaluation Of N-Dodecyl and N-tetradecyl Lactobionamides

General Experimental

The detergency of three lactobionamide samples (C12-, C14- and a one to one ratio of C12- and C14-lactobionamides) were evaluated using Tergotometer tests. The performance of the lactobionamides was compared with that of a commercial ethoxylated nonionic, Neodol 25-7 (alkyl chain lengths of 12–15 carbons with 7 oxyethyl polar groups). Because it would be expected that N-alkyl lactobionamides would be in a mixed active system, Tergotometer tests were also performed using ratios of linear alkylbenzene sulfonate (LaS)/lactobionamides of 25/75, 50/50, 75/25 and 90/10. The test cloths used for the majority of tests were Lever clay cloth (a 65/35 polyester/cotton cloth coated with an extremely hydrophobic di-tallow, dimethyl amine cation coated kaolinitic clay/quartz mixture), the VCD cloth (a 65/35 polyester/cotton blend, treated with fatty soil collected from vacuum cleaner bags), WKF 30C (polyester soiled with WFK standard soil) and WFK 30D (polyester soiled with pigment-/sebum) cloths. To test the blood stain removing ability of the C12-lactobionamide, the EMPa-116 cloth was used (a cotton cloth stained with milk and with Japanese ink, in addition to blood). non-phosphate, zeolite-built burkeite base powder was dosed over the side at about 1.85 g/l. Hardness was added as a 2:1 ratio of Ca:Mg. The system was kept a pH=10 and all Tergotometer tests were run for 15 minutes.

Improvement in detergency is measured by change in reflectance values ($\Delta R$) between the stained cloth and the cloth after treatment in the tergotometer, where reflectance values are measured by using a reflectometer and the value is obtained by the difference in reflectance before and after each washing.

EXAMPLE 19

As indicated above, samples of $C_{12}$, $C_{14}$ and 1:1 ratio $C_{12}$ to $C_{14}$ lactobionamides were evaluated against LEVER clay cloth at tergotometer conditions of 15° C. and 180 ppm salt (harsh conditions) in various ratios of anionic (LAS) to the lactobionamide (or commercially available Neodol) and results are set forth below:

| AR at Various Ratios of Anionic to Nonionic | | | | | |
|---|---|---|---|---|---|
| | 0/100 | 25/75 | 50/50 | 75/25 | 100/0 |
| $C_{12}$ | 11.2 | 10 | 9.2 | 10.3 | 12.2 |
| $C_{14}$ | 10.1 | 9.5 | 9.6 | 11.2 | 15 |
| 1:1 $C_{12}/C_{14}$ | 11.9 | 10.7 | 10.0 | 12 | 14 |
| Neodol 25-7 | 16.8 | 15.0 | 12.8 | 11.8 | 12.0 |

The results above suggest that pure LAS (i.e., 100/0 ratio) under the above conditions gives better detergency performance than each of the three lactobionamide samples (i.e., 0/100 ratio) and also of any of the samples made up of the various ratios of anionic to nonionics. Also, tested was a LAS/Neodol 25-7 system using the above conditions. Comparing the Neodol results to the lactobionamide results shows that, with respect to the Lever clay cloth, the Neodol 25-7 outperforms the lactobionamides in both the pure and mixed active systems. Both the low temperature and the high hardness used in these tests were suspected of affecting the results.

EXAMPLE 20

Sample of $C_{12}$, $C_{14}$ and 1:1 $C_{12}$ to $C_{14}$ lactobionamide and commercially available Neodol 25-7 were evaluated against VCD cloth at tergotometer conditions of 15° C. and 180 ppm salt (harsh conditions) in various ratios of anionic (LAS) to lactobionamide or to Neodol (the nonionic) and results are set forth below:

| AR of Various Ratios of ANionic:Nonionic | | | | | |
|---|---|---|---|---|---|
| | 0/100 | 25/75 | 50/50 | 75/25 | 100/0 |
| $C_{12}$ | 28.2 | 27.5 | 30 | 31 | 32 |
| $C_{14}$ | 29.8 | 29.5 | 31.5 | 33.5 | 33.8 |
| 1:1 $C_{12}/C_{14}$ | 29.8 | 29.5 | 29.5 | 32.5 | 32.5 |
| Neodol 25-7 | 25 | 25.5 | 31.0 | 31.5 | 32 |

Although the tests results that were obtained using VCD cloths (15° C. and 180 ppm hardness) did not show as significant a difference between the detergency of the lactobionamide samples and the LAS, the same trend of better results for the anionic surfactant held. But, unlike the results obtained using the Lever Clay cloth (see Example 14 above), the mixed LAS:lactobionamide systems performed at par or better than the LAS:Neodol system even at the harsh conditions of 15° C. and 180 ppm.

EXAMPLE 21

Samples of $C_{12}$ lactobionamide and Neodol 25-7 (nonionics) were evaluated against VCD cloths at tergotometer condition of 40° C., 120 ppm hardness and pH 9.7 (mild condition) in various ratios of anionic (LAS) to the nonionics and results set forth below:

| AR of Various Ratios of Anionic:Nonionic | | | | | |
|---|---|---|---|---|---|
| | 0/100 | 25/75 | 50/50 | 75/25 | 100/0 |
| $C_{12}$ lactobionamide | 33 | 34 | 34.9 | 36 | 35 |
| Neodol 25-7 | 32.8 | 32 | 33.0 | 34 | 35 |

These results show AR values obtained for various ratios of LAS:C12-lactobionamide and LAS:Neodol 25-7 using VCD cloths. The results for these mild conditions (40° C., 120 ppm) give results comparable to the same tests run at 15° C. and 180 ppm, that is the C12-lactobionamide performs at par or a little better than the Neodol 25-7 when tested in mixed nonionic/anionic systems.

EXAMPLE 22

Samples of $C_{12}$ lactobionamide and Neodol 25-7 (nonionics) were evaluated against EMPA-116 cloth at tergotometer conditions of 40° C. 120 ppm hardness and pH 9 7 (mild conditions) in various ratios of anionic (LaS) to the nonionics and results are set forth below:

| AR and Various Ratios of Anonic:nonionic | | | | | |
|---|---|---|---|---|---|
| | 0/100 | 25/75 | 50/50 | 75/25 | 100/0 |
| $C_{12}$ | 35 | 38 | 40 | 42 | 45 |
| Neodol 25-7 | 32.5 | 34 | 37 | 40 | 41 |

These results show the AR values obtained for various ratios of LaS:C12-lactobionamide and LAS:Neodol 25-7 on EMPA 116 test cloths (40° C., 120 ppm 2:1 Ca:Mg hardness). The results show that while C12-lactobionamide does not remove blood as well as LAS, it does a better job than Neodol 25-7 by about 3 AR units.

EXAMPLE 23

Samples of $C_{12}$ lactobionamide and Neodol 25-7 were evaluated against WKF30C and WFK30D cloths at tergotometer conditions of 40° C., 120 ppm hardness and pH of about 10 in various ratios of anionic (LAS) to the nonionics and these results are set forth below:

| AR at Various Ratios of Anionic:Nonionic | | | | | |
|---|---|---|---|---|---|
| | 0/10 | 27/75 | 50/50 | 75/25 | 100/0 |
| WFK30D | | | | | |
| $C_{12}$ | 15.0 | 18.0 | 21.8 | 25 | 26 |
| Neodol 25-7 | 12.0 | 16.0 | 19.5 | 22.8 | 26 |
| WFK30C | | | | | |
| $C_{12}$ | 4.0 | 6.2 | 9.0 | 10.9 | 11.0 |
| Neodol 25-7 | 2.0 | 4.8 | 7.0 | 9.5 | 11.0 |

As the results indicate, the anionic surfactant again outperforms all pure and mixed anionic/nonionic systems. again, the lactobionamide performs at par or slightly better than Neodol 25-7 in the mixed active and the all-nonionic systems.

In general the detergent evaluations show that the surfactants of the invention perform at a poor or better than the commonly available Neodol 25-7 against almost all substrates tested (except Lever clay). Moreover, in the example where parity was not met, cleaning was done under harsh conditions.

EXAMPLE 24

Use of Lactobionamides as Coactives in Detergent Bar Composition

A 1:1 mixture of $C_{12}$-$C_{14}$ lactobionamide co-surfactants were mixed with a fatty acyl isethionate active in a detergent bar composition having the following composition:

| COMPONENT | % BY WEIGHT |
|---|---|
| Fatty acid isethionate | 43 |
| Free fatty acids (coco and stearic acids) | 23 |
| $C_{12}$-$C_{14}$ (1:1) lactobionamide | 20 |
| Stearic acid | 8.5 |
| Titanium Dioxide | 0.5 |

| COMPONENT | % BY WEIGHT |
|---|---|
| Water | 5% |

All the components were combined and processed in a Braybender mixer for 40 minutes at 80°–85° C. The homogeneous mixture was then removed, allowed to cool, and pressed into bars. The bars were hard, cohesive, white solids. Initial qualitative experiments indicated that they lathered well with minimum of mushing.

EXAMPLE 25

Additional Information Regarding Detergency

Detergency performance was assessed in triolein removal experiments using Terg-O-Tometer. $^3$H radio-labelled triolein was used to assess soil removal; subsequent to the wash, 4×1 ml samples of wash liquor were removed from each pot and the activity determined using a liquid scintillation counter. Percentage detergency was calculated from the relationship:

$$\% \text{ Detergency} = \frac{A_w}{A_s} \times 100$$

where $A_w$ is the total activity in the wash liquor and $A_s$ is the level of activity originally applied to the cloth.

Wash conditions are given below:

| Apparatus | Terg-O-Tometer UR 7227 |
|---|---|
| Wash Time | 20 Minutes |
| Agitation | 70 rpm |
| Wash Liquid Volume | 500 mls |
| Active Dosage | 1 g/l |
| Salt Concentration | 0.05M |
| Test Cloth | Knitted Polyester |
| Soil Level | ca. 1.9% |

The Krafft Temperature of the N-alkyl lactobionamides is summarized in Table 2 below.

| | Krafft Temp. |
|---|---|
| N-dodecyl lactobionamide | 38 |
| N-tetradecyl lactobionamide | 46 |
| N-Coco lactobionamdie | <6 |

When these surfactants were mixed with $C_{12}EO_3$ synergistic detergency was obtained. For the tetradecyl derivative a sharp synergistic maximum was observed at a surfactant composition of 80/20=lactobionamide $C_{12}EO_3$.

EXAMPLE 26

Aldobionamide is Used in a Toilet Soap Bar

| Ingredients | % by Weight |
|---|---|
| $C_8$ to $C_{24}$ fatty acid | 5%–60% |
| Aldobionamide | 1–45% |
| Coactive other than Aldonamide | 0–50% |
| Alkyl or Aryl suflate or Sulfonate | 0–5% |
| Moisturizer (e.g. Sorbitol or Glycerin) | 0.1–10% |
| Water soluble polymer (e.g. Cellulase or Poly-acrylates) | 0–10% |
| Sequestering agents (e.g. citrate) | 0.1–0.5% |
| Dye stuff | <0.1% |
| Optical brighteners | <0.1% |
| Whitening agents | 0.1–0.4% |
| Fragrance | 0.1–2.0% |
| Water | Balance |

EXAMPLE 27

Aldobionamide is Used in a Facial/Body Cleanser Composition

| Ingredients | % by Weight |
|---|---|
| C8–24 fatty acid salt (e.g. triethanolamine) | 1–45% |
| Aldobionamide | 10–75% |
| Alkyl or aryl sulfate or sulfonate | 0–20% |
| Coactive surfactant (e.g. cocoamidobetaine) | 1–15% |
| Moisturizer (e.g. sorbitol) | 0.1–15% |
| Refattying alcohol | 0.5–5% |
| Water soluble polymer | 0–10% |
| Thickener | 0–15% |
| Conditioner (e.g. quaternized cellulose) | 0–0.5% |
| Sequestering agents (e.g. citrate) | 0.1–0.4% |
| Dye stuff | <0.1% |
| Optical brighteners | <0.1% |
| Whitening agents | 0.1–0.4% |
| Fragrance | 0.1–3.0% |
| Preservatives | 0–0.2% |
| Water | Balance |

EXAMPLE 28

Aldobionamide is Used in a Toothpaste Composition

| Ingredients | % by Weight |
|---|---|
| Synthetic surfactants (sodium lauryl sulfate) | 1.5% |
| Aldobionamide | 1–10% |
| Alkyl or aryl sulfate or sulfonate | 0–1% |
| Abrasive (e.g. silic acid/ $CaCO_3$) | 20–55% |
| Active ingredients (e.g., Pyrophospates) | 0.1–2% |
| Humectant (glycerin, sorbitol) | 10–45% |
| Thickeners (cellulose derivatives) | 0–3% |
| Sequestering agents (e.g. citrate) | 0.1–0.4% |
| Flavoring agents | 0.5–2% |
| Sweeteners | <0.5% |
| Dye stuff | <0.1% |
| Water | Balance |

EXAMPLE 29

Cyclic Aldobionamide Versus Linear Saccharide

In order to show that the aldobionamides (i.e., having at least two saccharide units) of the invention are advantageous relative to the linear saccharides (e.g., gluconomide), applicants measured the Krafft points of $C_{10}$, $C_{12}$ and $C_{14}$ gluconamides and compared those to $C_{10}$, $C_{12}$ and $C_{14}$ lactobionamide. Specifically, 1 gram surfactant was measured in 99 grams water (1% surfactant solution) and the results set forth below:

| Gluconamide* | | Lactobionamide | |
|---|---|---|---|
| Alkyl Chain Length | Krafft Point (1% concentration) | Alkyl Chain Length | Krafft Point (1% concentration) |
| $C_{10}$ | 84° C. | $C_{10}$ | 0° C. |
| $C_{12}$ | 95° C. | $C_{12}$ | 38° C. |
| $C_{14}$ | >100° C. | $C_{14}$ | 46° C. |

*gluconamide structure is as follows:

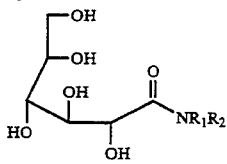

wherein $R_1$ and $R_2$ are defined as for the aldobionamides of the invention.

This data clearly shows that the Krafft point of the lactobionamide (i.e., measure of solubility) is much lower than that of the corresponding chain length gluconamide.

While not wishing to be bound by theory, this is believed to be a function, at least in part, if the fact that the linear gluconamide packs more closely and is therefore less soluble in solution. The lower Krafft point is also associated with higher foaming.

EXAMPLE 30

Shampoo Using Gluconamides and Lactobionamides

To further show the difference in solubility between the aldobionamides of the invention and linear saccharides such as gluconamide, applicants made shampoo compositions comprising the following:

| Shampoo Compositions | |
|---|---|
| Compound | Weight % |
| (I) | |
| Sodium dodecylsulfate | 14% |
| Sodium chloride | 2% |
| N-dodecyl Lactobionamide | 4% |
| Water | 80% |
| (II) | |
| Sodium dodecyl sulfate | 14% |
| Sodium chloride | 2% |
| N-dodecyl Lactobionamide | 8% |
| Water | 76% |
| (III) | |
| Sodium dodecyl sulfate | 14% |
| Nacl | 2% |
| N-dodecyl glucanamide | 4% |
| Water | 80% |

Composition (I) and (II) which contain coco lactobionamide (4% and 8%) gave homogeneous clear viscous liquid shampoo, while composition (III) which contain N-dodecyl glucanamide gave cloudy non viscous liquid shampoo resulting from precipitation of the N-dodecyl glucanamide which is believed to be due to high Krafft temperature.

It can also be seen that even up to 8% lactobionamide was readily soluble (versus 4% gluconamide which was not soluble),

We claim:

1. A personal product composition comprising an aldobionamide and a surfactant selected from the group consisting of anionic surfactants, nonionic surfactants and mixtures thereof.

2. A personal product composition according to claim 1, wherein the composition is a toilet bar soap.

3. A composition according to claim 2, comprising the following:

| Ingredients | % by Weight |
|---|---|
| $C_8$-$C_{24}$ fatty acid | 5-60% |
| Aldobionamide | 1-45% |
| Alkyl or aryl sulfate or sulfonate | 0-5% |
| Coactive other than Aldobionamide | 0-50% |
| Sorbitol | 0.1-10% |
| Cellulose | 0-10% |
| Sequestering agent | 0.1-0.5% |
| Water | to Balance. |

4. A personal product composition according to claim 1, wherein the composition is a facial/body cleanser.

5. A composition according to claim 4, comprising the following:

| Ingredients | % by Weight |
|---|---|
| $C_8$-$C_{24}$ fatty acid salt | 1-45% |
| Aldobionamide | 10-75% |
| Alkyl or aryl sulfate or sulfonate | 0-20% |
| Cocamidobetaine | 1-15% |
| Sorbitol | 0.1-15% |
| Refattying alcohol | 0.5-5% |
| Water soluble polymer | 0-10% |
| Thickener | 0-15% |
| Quaternized cellulose | 0-0.5% |
| Citrate | 0.1-0.4% |
| Water | to Balance. |

6. A composition according to claim 1, wherein the composition is a shampoo.

7. A composition according to claim 6 comprising: (all percentages by weight)
 (1) Aldobionamide 5-15%;
 (2) Anionic coactive 0-10%;
 (3) Amphoteric coactive 0-10%;
 (4) Lauramide monoethanolamide 0-5%;
 (5) Thickener 0-5%;
 (6) Fragrance 0-2%;
 (7) Preservative 0-1%; and
 (8) Remainder water.

8. A composition according to claim 1, wherein the composition is a conditioner composition.

9. A composition according to claim 1, wherein the composition is a cosmetic composition.

10. A composition according to claim 1, wherein the composition is a light duty liquid detergent.

11. A composition according to claim 1, wherein the composition is shaving cream or shaving lotion.

12. A composition according to claim 1, wherein the composition is a shower gel.

13. A personal product composition according to claim 1, wherein the aldobionamide has the structure set forth below:

wherein A is a sugar moiety which is an aldobionic acid except that it does not contain the OH group normally extending from the carbonyl group on the aldonic acid;

NR₁R₂ is attached where the hydroxyl group on the aldobionic acid would normally be found; and R₁ and R₂ are the same or different and are selected from the group consisting of hydrogen, aliphatic hydrocarbons, aromatic radicals, cycloaliphatic radicals, amino acid esters, ether amines and mixtures thereof except that R₁ and R₂ cannot be hydrogen at the same time.

14. A composition according to claim 13 wherein, on the aldobionamide, R₁ is hydrogen and R₂ is an alkyl group having 8 to 24 carbons.

15. A composition according to claim 13 wherein, on the aldobionamide, A is a disaccharide sugar group forming the compound which is an aldonic acid except for the OH group.

16. A composition according to claim 15, wherein the aldobionamide is a lactobionamide having the structure

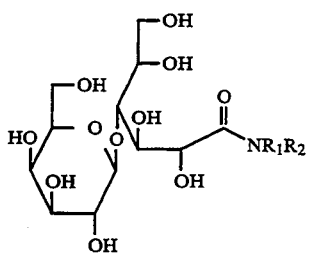

wherein R₁ and R₂ are the same or different and are selected from the group consisting of hydrogen, aliphatic hydrocarbons, aromatic radicals, cycloaliphatic radicals, amino acid esters, ether amines and mixtures thereof, except that R₁ and R₂ cannot be hydrogen at the same time.

17. A composition according to claim 16 wherein, on the aldobionamide, R₁ is hydrogen and R₂ is an alkyl group having 8 to 24 carbons.

18. A composition according to claim 13, wherein the aldobionamide is maltobionamide having the structure:

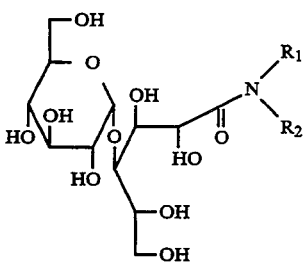

wherein R₁ and R₂ are the same or different and are selected from the group consisting of hydrogen, aliphatic hydrocarbons, aromatic radicals, cycloaliphatic radicals, amino acid esters, ether amines, and mixtures thereof, except that R₁ and R₂ cannot be hydrogen at the same time.

19. A composition according to claim 18 wherein, on the aldobionamide, R₁ is hydrogen and R₂ is an alkyl group having 8 to 24 carbons.

20. A detergent composition comprising an aldobionamide and a surfactant selected from the group consisting of anionic surfactants, nonionic surfactants and mixtures thereof.

21. A composition according to claim 20 wherein the aldobionamide has the structure:

ANR₁R₂ wherein A is a sugar moiety which is an aldobionic acid except that it does not contain the OH group normally extending from the carbonyl group on the aldobionic acid;

NR₁R₂ is attached where the hydroxyl group on the aldobionic acid would normally be found; and R₁ and R₂ are the same or different and are selected from the group consisting of hydrogen, aliphatic hydrocarbons, aromatic radicals, cycloaliphatic radicals, amino acid esters, ether amines, and mixtures thereof, except that R₁ and R₂ cannot be hydrogen at the same time.

22. A composition according to claim 21 wherein, on the aldobionamide, R₁ is hydrogen and R₂ is an alkyl group having 8 to 24 carbons.

23. A composition according to claim 21 wherein, on the aldobionamide, A is a disaccharide sugar group forming the compound which is an aldonic except for the OH group.

24. A composition according to claim 23 wherein the aldobionamide is a lactobionamide having the structure:

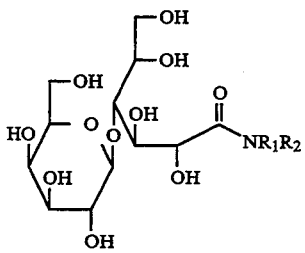

R₁ and R₂ are the same or different and are selected from the group consisting of hydrogen, aliphatic hydrocarbons, aromatic radicals, cycloaliphatic radicals, amino acid esters, ether amines, and mixtures thereof, except that R₁ and R₂ cannot be hydrogen at the same time.

25. A composition according to claim 24 wherein, on the aldobionamide, R₁ is hydrogen and R₂ is an alkyl group having 8 to 24 carbons.

26. A detergent composition according to claim 20, which is a liquid composition as follows:
(1) 5 to 70% by weight of a detergent active system comprising lactobionamide and further comprising a surfactant selected from the group consisting of anionic surfactants, nonionic surfactants and mixtures thereof;
(2) 0 to 50% by weight builder;
(3) 0 to 40% by weight electrolyte;
(4) 0.01 to 5% by weight enzyme;
(5) 0.1 to 5% by weight enzyme stabilizer;
(6) 0–20% 0 to 20% by weight phase regulant; and
(7) remainder water and minors.

27. A detergent composition according to claim 20, which is a powdered composition as follows:
(1) 5 to 40% by weight of a detergency active system comprising lactobionamide and further comprising a surfactant selected from the group consisting of anionic surfactants, nonionic surfactants and mixtures thereof;
(2) 0 to 40% by weight builder;
(3) 0 to 30% by weight buffer salts;
(4) 0 to 30% by weight sulfate;
(5) 0 to 20% by weight bleach system;
(6) 0–40% 0 to 40% by weight enzyme; and
(7) minors plus water to 100%.

* * * * *